(12) United States Patent
Cohen et al.

(10) Patent No.: US 10,646,173 B2
(45) Date of Patent: May 12, 2020

(54) PEDIATRIC SUPPORT SYSTEM AND METHOD FOR MEDICAL IMAGING

(71) Applicant: General Electric Company, Schenectady, NY (US)

(72) Inventors: Adam Israel Cohen, Milwaukee, WI (US); William Harrison Mann, Oconomowoc, WI (US); Adam Gregory Pautsch, Oconomowoc, WI (US); Joshua Thomas Lamb, Oconomowoc, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 274 days.

(21) Appl. No.: 15/695,172

(22) Filed: Sep. 5, 2017

(65) Prior Publication Data
US 2019/0069854 A1 Mar. 7, 2019

(51) Int. Cl.
*A47B 13/00* (2006.01)
*A61B 6/04* (2006.01)
(Continued)

(52) U.S. Cl.
CPC ............ *A61B 6/0428* (2013.01); *A61B 6/032* (2013.01); *A61B 6/037* (2013.01); *A61G 7/103* (2013.01);
(Continued)

(58) Field of Classification Search
CPC ................ A61G 7/103; A61G 2200/14; A61G 2210/50; A61B 6/032; A61B 6/037;
(Continued)

(56) References Cited

U.S. PATENT DOCUMENTS 3,215,834 A * 11/1965 Tayman ............... A61B 6/0421
378/174
3,892,399 A * 7/1975 Cabansag ........... A61B 6/0421
378/174

(Continued)

FOREIGN PATENT DOCUMENTS

CN 106214174 A 12/2016
DE 7013144 U 4/1974
(Continued)

OTHER PUBLICATIONS

PCT/US2018/047245; International Search Report and Written Opinion; dated Nov. 28, 2018, pp. 1-13.
U.S. Appl. No. 15/359,159, filed Nov. 22, 2016, Cohen et al.

*Primary Examiner* — Nicholas F Polito
*Assistant Examiner* — Morgan J McClure
(74) *Attorney, Agent, or Firm* — Fletcher Yoder, P.C.

(57) ABSTRACT

A pediatric patient support system is provided. The system includes a support extension configured to be removably coupled to a cradle of a table, wherein the support extension includes radial supports extending in a radial direction relative to a longitudinal axis of the cradle. The system includes a pair of rods, wherein each rod is coupled to a respective radial support and extends substantially parallel to the longitudinal axis. The system includes a patient support disposed between and coupled to the rods, the patient support being configured to support a pediatric patient, wherein the patient support is configured to move axially relative to the longitudinal axis along the rods to move the pediatric patient in and out of a central bore of a medical imaging system.

20 Claims, 6 Drawing Sheets

(51) Int. Cl.
*A61G 7/10* (2006.01)
*A61B 6/03* (2006.01)

(52) U.S. Cl.
CPC ............ *A61B 6/04* (2013.01); *A61G 2200/14* (2013.01); *A61G 2210/50* (2013.01)

(58) Field of Classification Search
CPC ........... A61B 6/04; A61B 5/0555; A61B 5/70; A61B 5/704; A61B 6/0421; A61B 6/0428
See application file for complete search history.

(56) References Cited

U.S. PATENT DOCUMENTS

| | | | | |
|---|---|---|---|---|
| 4,779,858 A * | 10/1988 | Saussereau | ......... | A61B 6/0421 378/209 |
| 4,838,275 A * | 6/1989 | Lee | ...... | A61B 5/0205 600/483 |
| 5,018,712 A * | 5/1991 | Schaefer | ................ | A61B 6/04 5/607 |
| 5,281,232 A * | 1/1994 | Hamilton | ............ | A61B 6/0421 600/429 |
| 5,349,956 A * | 9/1994 | Bonutti | ............... | A61B 5/0555 5/601 |
| 6,684,095 B1 * | 1/2004 | Bonutti | ............... | A61B 5/0555 5/601 |
| 2001/0012914 A1 * | 8/2001 | Kuth | ................... | A61B 5/0555 600/415 |
| 2005/0059877 A1 * | 3/2005 | Falbo, Sr. | ............... | A61B 6/04 600/407 |
| 2006/0197530 A1 * | 9/2006 | Damadian | ........... | A61B 5/0555 324/318 |
| 2007/0050908 A1 * | 3/2007 | Kogan | ............... | A61B 6/0457 5/128 |
| 2009/0027053 A1 * | 1/2009 | Decke | ................. | A61B 5/0555 324/318 |
| 2011/0119829 A1 * | 5/2011 | Skripps | ............... | A61B 6/0421 5/601 |
| 2012/0324648 A1 * | 12/2012 | Amano | ................. | A61B 6/037 5/601 |
| 2013/0096417 A1 * | 4/2013 | Hering | ................ | A61B 5/0555 600/415 |
| 2013/0150656 A1 * | 6/2013 | Falk | ..................... | A61B 5/0555 600/22 |
| 2014/0083436 A1 * | 3/2014 | Pettinato | ............. | A61B 6/0428 128/870 |
| 2014/0357981 A1 * | 12/2014 | Dumoulin | ........... | A61B 5/0555 600/415 |
| 2017/0181912 A1 * | 6/2017 | Rapoport | ............ | A61G 11/005 |
| 2017/0196477 A1 * | 7/2017 | Wehner | ............ | A61G 13/101 |
| 2017/0212192 A1 * | 7/2017 | Rapoport | ............ | G01R 33/341 |

FOREIGN PATENT DOCUMENTS

| | | | | |
|---|---|---|---|---|
| FR | 2523433 A1 | 9/1983 | | |
| JP | S5676938 | * | 6/1981 | ............... A61B 6/04 |
| JP | S5676938 A | | 6/1981 | |

* cited by examiner

PEDIATRIC SUPPORT SYSTEM AND METHOD FOR MEDICAL IMAGING

BACKGROUND

The subject matter disclosed herein relates to medical imaging and, in particular, to a pediatric support system for supporting a patient for medical imaging.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the emission of gamma radiation, to acquire data and to construct images or otherwise represent the observed internal features of the patient.

Traditionally, medical imaging systems, such as a computed tomography (CT) imaging system or a CT/positron emission tomography (PET) imaging system, include a gantry and a patient table. The patient table needs to be as transparent as possible to X-rays used by the CT imaging system and the gamma rays used by the PET imaging system. As a result, the tables are constructed of thin, composite materials which need to support several hundred pounds of weight. The patient table includes a cantilevered patient support (e.g., cradle or pallet) that extends from the table into the gantry bore. However, patient supports having a cantilevered configuration generally have a vertical thickness that may attenuate the radiation (e.g., X-rays and gamma radiation) and induce undesirable noise during medical imaging procedures. For example, the vertical thickness of the cantilevered patient support may have a large amount of material to fill a large cross-sectional area such that the cantilevered patient support has sufficient strength to support patients of various size and weight. As such, radiation dose efficiency and image quality may be affected by the vertical thickness of the cantilevered patient table. In particular, infants and small toddlers may be exposed to excessive radiation.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a pediatric patient support system is provided. The pediatric patient support system includes a support extension configured to be removably coupled to an end of a cradle of a table, wherein the support extension includes a pair of radial supports extending in a radial direction relative to a longitudinal axis of the cradle. The pediatric patient support system also includes a pair of rods, wherein each rod of the pair of rods is coupled to a respective radial support of the pair of radial supports and extends substantially parallel to the longitudinal axis. The pediatric patient support system further includes a patient support disposed between and coupled to the pair of rods, the patient support being configured to support a pediatric patient, wherein the patient support is configured to move axially relative to the longitudinal axis to move the pediatric patient in and out of a central bore of a medical imaging system.

In accordance with a second embodiment, a method for utilizing a pediatric patient support system is provided. The method includes coupling a support extension to an end of a cradle of a table, wherein the support extension includes a pair of radial supports extending in a radial direction relative to a longitudinal axis of the cradle. The method also includes coupling a respective rod to each radial support of the pair of radial supports so that each respective rod extends substantially parallel to the longitudinal axis. The method further includes coupling a patient support to each respective rod so that the patient support is disposed between the respective rods, the patient support being configured to support a pediatric patient, wherein the patient support is configured to move axially relative to the longitudinal axis to move the pediatric patient in and out of a central bore of a medical imaging system.

In accordance with a third embodiment, a pediatric patient support system is provided. The pediatric patient support system includes a support extension configured to be removably coupled to an end of a cradle of a table via a protrusion of the support extension being inserted within a slot in the end of the cradle, wherein the support extension includes a pair of radial supports extending above the cradle in a radial direction relative to a longitudinal axis of the cradle. The pediatric patient support system also includes a pair of rods configured to partially extend into a central bore of a medical imaging system when the pediatric patient support system is coupled to the cradle, wherein each rod of the pair of rods is extends through a respective radial support of the pair of radial supports and extends substantially parallel to the longitudinal axis. The pediatric patient support system further includes a patient support disposed between and coupled to the pair of rods, the patient support being configured to support a pediatric patient, wherein the patient support is configured to move axially relative to the longitudinal axis along the pair of rods to move the pediatric patient in and out of the central bore. The support extension, the pair of rods, and the patient support are configured to be solely supported by the cradle of the table.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As described herein, in certain instances medical imaging systems, such as a computed tomography (CT) imaging system or a CT/positron emission tomography (PET) imaging system, include a patient table that includes a cantilevered patient support (e.g., cradle or pallet) that extends from the table into a gantry bore. However, a configuration of the cantilevered patient support may attenuate radiation (e.g., X-ray and gamma radiation) used to image a patient. For example; the cantilevered patient support may have a large vertical thickness (e.g., cross-sectional area) such that the cantilevered patient support has sufficient material density to provide a strength suitable to support patients of various size and weight. The material density of the cantilevered patient support may attenuate the radiation (e.g., by absorbing and/or scattering the radiation) and increase noise levels during medical imaging. Accordingly, radiation dose efficiency may be decreased and an amount of radiation used during medical imaging may need to be increased to account for the attenuated radiation such that the patient receives a radiation dose suitable for producing a desired image quality. In particular, infants and small toddlers may be exposed to excessive radiation due to compensation for radiation attenuated by the cantilevered patient support.

Accordingly, it may be desirable to use a patient support specifically configured for infants and small toddlers that improves radiation dose efficiency and noise levels. Disclosed herein is a pediatric patient support system having a hammock-like configuration that may facilitate pediatric patient transfer to and from the medical imaging system and may also reduce attenuation of the radiation and noise levels during medical images compared to cantilevered patient support systems. The pediatric patient support system may also reduce the amount radiation needed (e.g., by up to approximately 33 percent) to scan the pediatric patient compared to cantilevered patient support systems.

Figure 1:
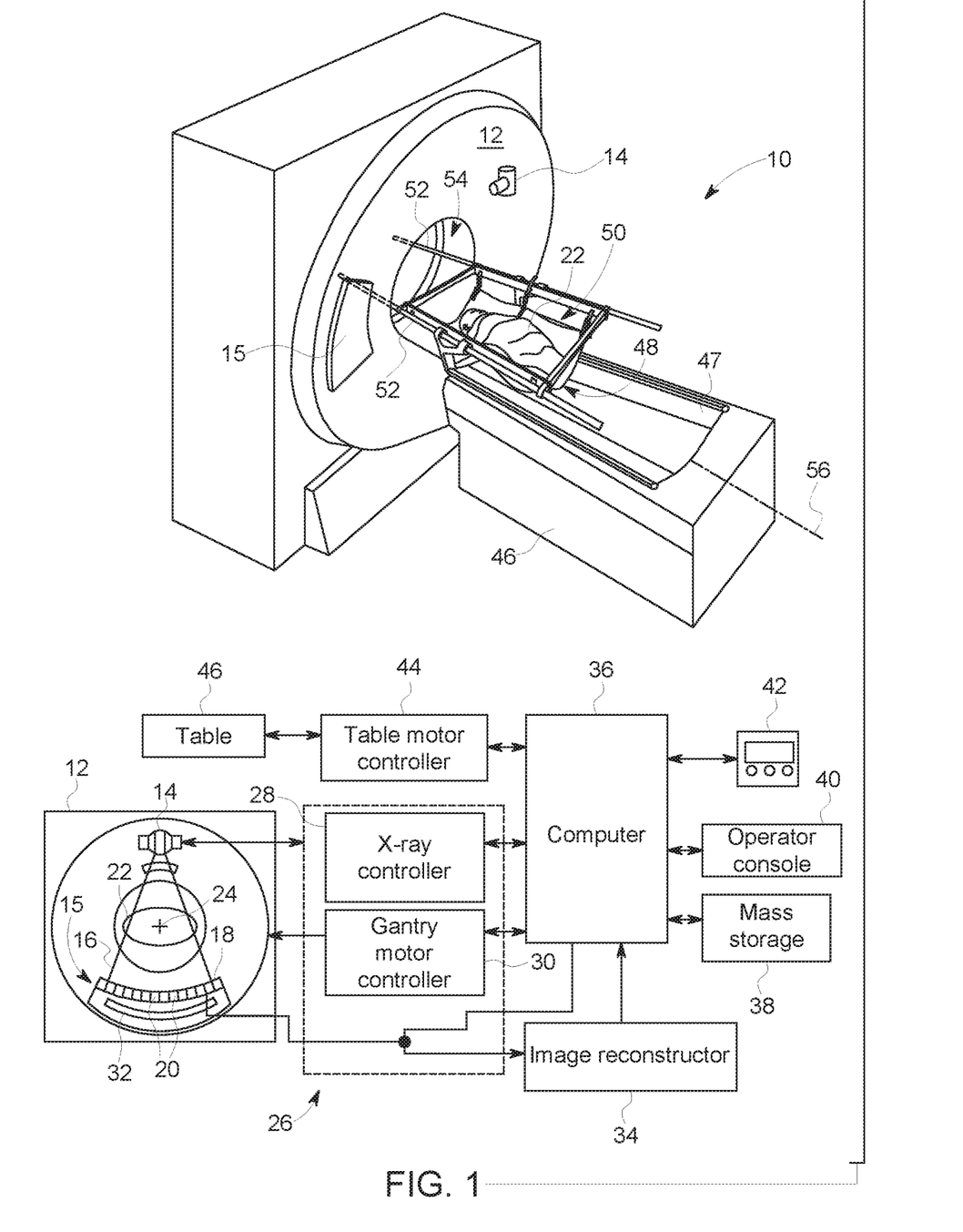
FIG. 1 is a combined pictorial view and block diagram of a computed tomography (CT) imaging system as discussed herein.

Although the following embodiments are discussed in terms of a computed tomography (CT) imaging system, the embodiments may also be utilized with other imaging systems (e.g., PET, CT/PET, SPECT, nuclear CT, etc.). With the foregoing in mind FIG. 1 is a diagram of a CT imaging system 10 that may be used for medical imaging procedures. The CT imaging system 10 includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22 (e.g., pediatric patient such as an infant or small toddler), and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to the X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls movement of a motorized table 46 (and/or patent support such as a cradle 47 or pallet) to position the patient relative to the gantry 12 (e.g., adjust height of table 46). In certain embodiments, the controller 44 may control movement of portions of a pediatric patient support system 48 (e.g., patient support 50) along rods 52 (e.g., carbon fiber tubes) via a motorized system (e.g., step motor) into and/or out of a gantry opening or bore 54 of the medical imaging system 10. The pediatric patient support system 48 includes the patient support 50 that retains and secures the pediatric patient 22 during the imaging procedure. As described in greater detail below, the pediatric patient support system 48 may include rods 52 (or patient support beams) that secure and enable linear movement (axially relative to a longitudinal axis 56 of the cradle 47 and table 46) of the patient support 50 along the rods 52 during the imaging procedure.

The pediatric patient support system 48 may be removably attached (e.g., via support extension or accessory) to an end of the cradle 47 as described in greater detail below. The cradle 47 of the table 46 solely supports the entire pediatric patient support system 48. The patient support 50 may be removably attached (e.g., directly or indirectly) to the rods 52. The patient support 50 with the patient 22 may be moved in and out of the bore 54. In certain embodiments, the patient support 50 is manually moved (e.g., slid) via a sliding mechanism that the patient support 50 is coupled to. In other embodiments, the patient support 50 may be moved via a motorized system. Once the pediatric patient 22 is placed on the patient support 48, a height of the table 46 and/or cradle 47 is adjusted. Accordingly, the patient 22 may be suspended in the patient support 50 (e.g., similar to a hammock) before moving the patient 22 into the bore 54 for the imaging procedure. During imaging of the patient 22 in the bore 54, all portions of the table 46 remains outside the bore 54 and the cradle 47 remains outside the path of the radiation. Since the table 46 remain outside the bore 54 and the cradle 47 remains outside the path of the radiation during imaging, a lower dose of radiation (e.g., up to approximately 33 percent less) may be utilized on the pediatric patient 22 since less radiation will be attenuated, while still maintaining image quality.

Figure 2:
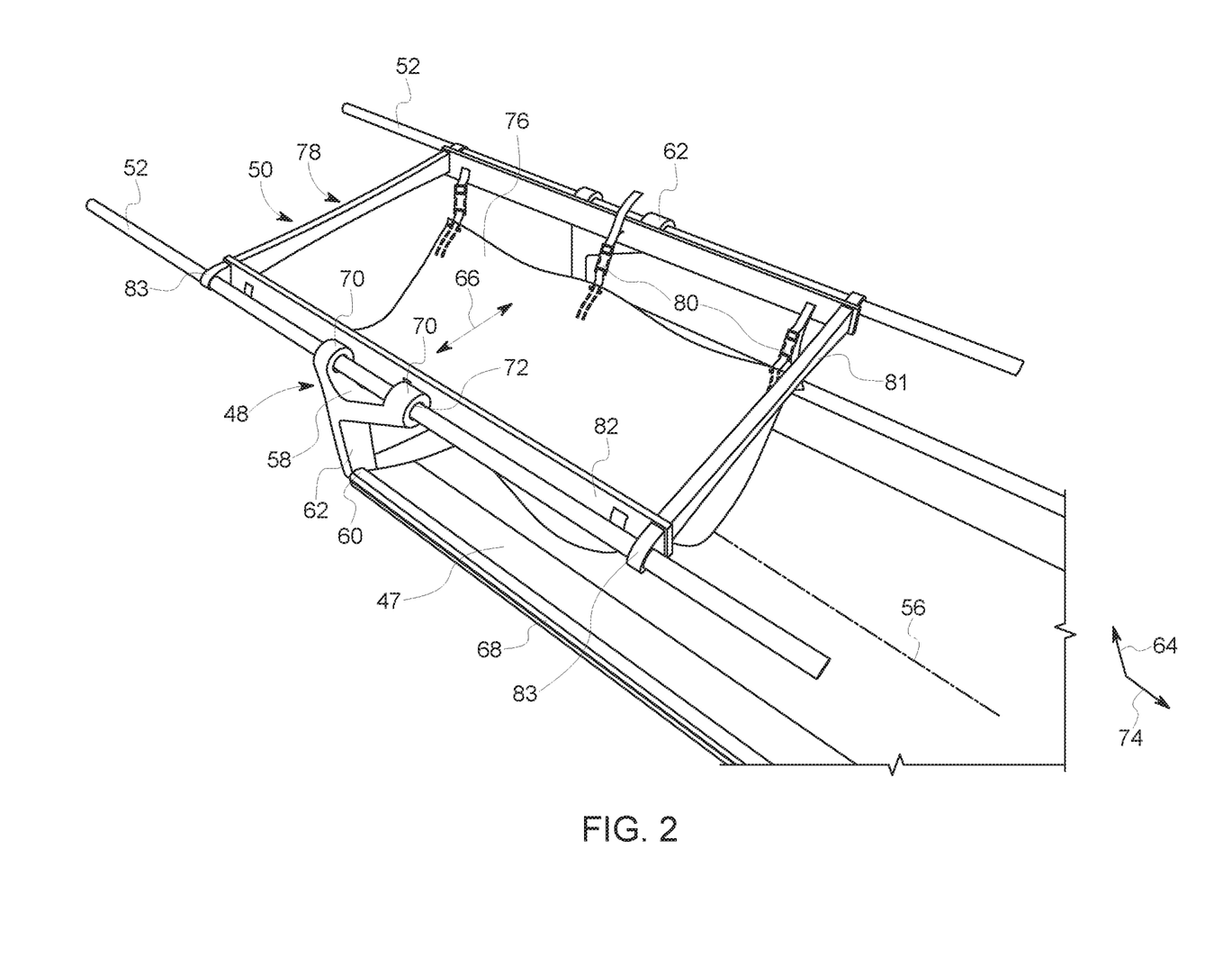
FIG. 2 is a perspective view of an embodiment of a pediatric patient support system for positioning and supporting a pediatric patient within a bore of a gantry.

FIG. 2 is a perspective view of an embodiment of the pediatric patient support system 48 for positioning and supporting the pediatric patient 22 within the bore 54 of the gantry 12. The pediatric patient support system 48 includes a support extension or accessory 58, the rods 52, and the patient support 50. The support extension 58 removably couples the pediatric patient support system 48 to an end 60 (e.g., longitudinal end) of the cradle 47. In certain embodiments, the support extension 58 may include a protrusion that inserts within a slot disposed within the end 60 of the cradle 47. In other embodiments, the support extension 58 may couple to the end 60 via a different mechanism. In other embodiments, the support extension may be coupled to the cradle 47 via a different mechanism (e.g., on top of the cradle 47). For example, lateral edges 68 of the cradle 47 may include channels configured to receive portions of the support extension 58. For example, the support extension 58 may be clamped on to cradle 47 via the channels or slid onto the cradle 47 channels. In certain embodiments, these channels in the lateral edges 68 may also be used to receive a rod that is coupled to fabric or webbing at end with the other end of the fabric coupled to the rods 52 to relieve radial supports 62 of some forces when the patient support 50 is extended into the bore 54. The support extension 58 supports both the rods 52 and the patient support 50. The shape of the support extension 58 may vary. As depicted, the support extension 58 includes a pair of radial supports 62 that extend radially 64 (e.g., relative to longitudinal axis 56) above the cradle 47. The radial supports 62 are spaced apart from each other in a direction 66 crosswise to both the longitudinal axis 56 and the radial direction 64. In particular, the radial supports 62 are disposed adjacent lateral edges 68 of the cradle 47. Each radial support 62 splits in the radial direction 64 into multiple supports 70 (e.g., forming a Y-shape). Each support 70 includes a hole or opening 72 to receive a respective rod 52. The holes 72 of the supports 70 of a respective radial support 62 are aligned to receive the same rod 52. When the rods 52 are coupled to the supports 62 the rods 52 are substantially parallel (e.g., ±10 degrees) within the longitudinal axis 56.

The rods 52 may be carbon fiber tubes. A portion of the rods 52 axially 74 (e.g., relative to the longitudinal axis 56) extend through the openings 72 of the respective supports 70. The rods 52 are configured to extend (e.g., axially 74) into the bore 54 of the medical imaging system 10. The rods 52 are spaced apart from each other in the direction 66 to be outside the imaging volume within the bore 54. The rods 52 support the patient support 50 and the pediatric patient 22 between the rods 52.

The patient support 50 includes a backing 76 that abuts against the patient 22 when the pediatric patient 22 is loaded onto the patient support 50 and provides support for the patient 22 during the imaging procedure. By way of non-limiting example, the backing 76 may be manufactured from materials that are flexible, breathable, and provide patient comfort. Moreover, the backing 76 may include materials that have a suitable tensile strength to support infants and small toddlers, low X-ray attenuation (e.g., attenuate between approximately 0 percent and 10 percent of the beam of X-rays 16 or other suitable medical imaging radiation), and be readily cleaned (e.g., wiped, laundered, sterilized) for reuse. By way of non-limiting example, the backing 76 may include a fabric such as nylon, cotton, canvas, polyester, or any other suitable heavy duty fabric. In certain embodiments, the backing 76 may be coated with an anti-microbial material to maintain sterility.

The backing 76 may be coupled to the rods 52 (e.g., directly or indirectly) to secure and suspend the patient 22 during the imaging procedure. As depicted, the backing 76 is coupled to a sliding structure 78. The backing 76 may include attachment features that secure the backing 76 to the sliding structure 78. For example, the backing 76 may include a plurality of fasteners 80 that may be removably attached to the sliding structure 78 to secure the backing 76 to the structure 78. In certain embodiments, the backing 76 may be directly coupled to the rods 52 via the fasteners 80.

The plurality of fasteners 80 may include any suitable fastener that secures the backing 76 to the sliding structure (or rods 52) and has a suitable tensile strength such that the pediatric patient 22 may be safely suspended and transported into and out of the bore 55 of the medical imaging system 10. In one embodiment, the plurality of fasteners 80 may include a Velcro® belt or any other suitable belt that may wrap around at least a portion of the sliding mechanism 78 (or rod 52) to secure the backing 76. In another embodiment, the plurality of fasteners 80 may include hooks that may be hooked onto the sliding mechanism 78 (or rods 52) or may be inserted into complementary openings on the sliding mechanism 78 (or rods 52) to secure the backing 76 to the sliding mechanism 78 (or rods 52). In certain embodiments, the plurality of fasteners 80 may be coupled to complementary fasteners on the sliding mechanism 78 (or rods 52) (e.g., a snap fit connection) to secure the backing 76 to the sliding mechanism 78 (or rods 52). In other embodiments, the plurality of fasteners 80 may include a combination of different fasteners (e.g., belts, hooks, snap-fit fasteners, etc.) to secure the backing 76 to the sliding mechanism 78 (or rods 52). In certain embodiments, buckles may be integrated into a swaddle cloth (e.g., acting as or replacing the backing 76) for the patient support 50.

As depicted, the sliding mechanism 78 includes cross supports 81 coupled to lateral supports 82. The supports 81, 82 may be spaced apart from each other in the directions 66, 74 to be outside the imaging volume within the bore 54. The sliding mechanism 78 enables the patient support 50 with the patient 22 to be moved axially 74 along the rods 52 in and out of the bore 54 of the medical imaging system 10. When the patient 22 is within the bore 54, only a portion of the rods 52 and the patient support 50 are also disposed within the bore 54. The sliding mechanism 78 enables the patient support 50 (and patient 22) to be moved manually. As depicted, the sliding mechanism 78 includes stops 83 that abut against the supports 70 to keep the sliding mechanism 78 and patient support 50 from sliding beyond a certain point along the rods 52 into or out of the bore 54. In certain embodiments, the stops 83 may be disposed on the rods 52 to block movement of the sliding mechanism 78 and/or patient support 50 beyond certain points along the rods 52. In certain embodiments, the patient support 50 (with or without the sliding mechanism) may be moved mechanically (e.g., via a motorized system, for example, including a step motor) or pneumatically.

Figure 3:
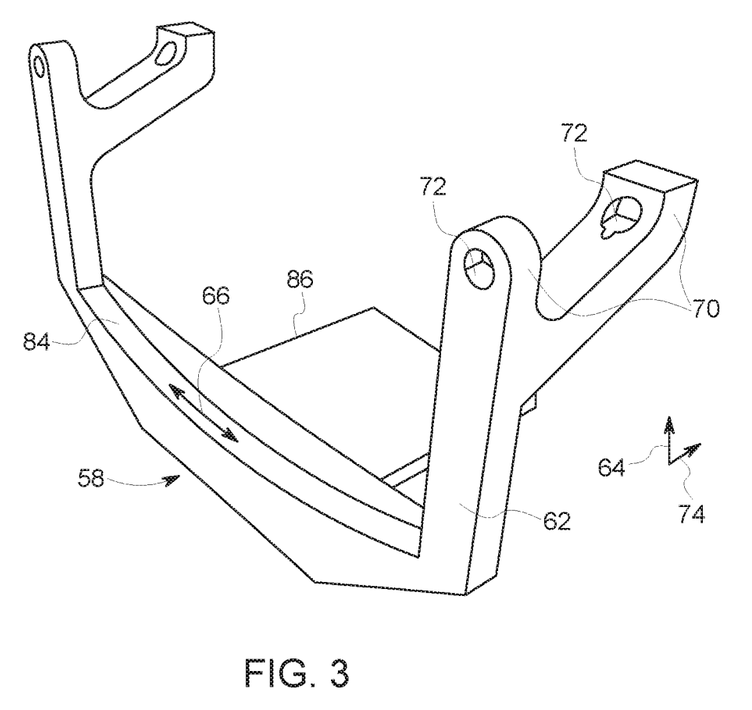
FIG. 3 is a perspective view of an embodiment of a support extension of the pediatric patient support system of FIG. 2.

FIG. 3 is a perspective view of an embodiment of the support extension 58 of the pediatric patient support system 48 of FIG. 2. In certain embodiments, the shape of the support extension may vary from the shaped depicted in FIG. 3. In general, the support extension 58 is as described above. As depicted, the support extension 58 includes a cross support 84 extending in the direction 66 between the radial supports 62. A protrusion 86 extends axially 74 from the cross support 84. The protrusion 86 inserts within a slot 88 (see FIGS. 4 and 5) disposed within the end 60 of the cradle 47 to couple the pediatric patient support system 48 to the cradle 47. The cross support 84 abuts the end 60 of the cradle 47 when the protrusion 86 is inserted within the slot 88. In other embodiments, the support extension 58 may couple to the end 60 via a different mechanism. In certain embodiments, the support extension 58 may be disposed on or coupled to a top surface of the cradle 47 adjacent the end 60.

Figure 4:
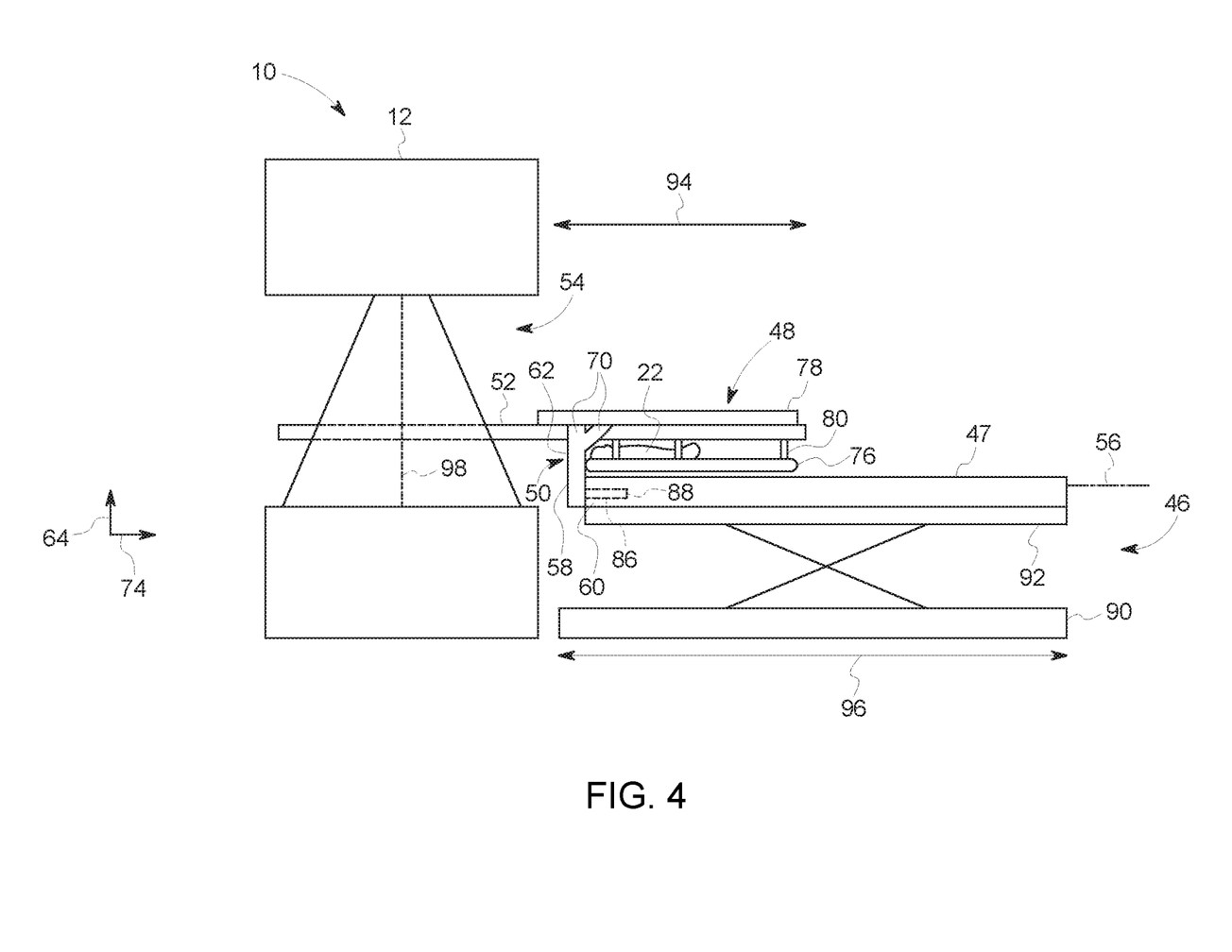
FIG. 4 is a schematic diagram of an embodiment of the pediatric patient support system of FIG. 2 being utilized to position a pediatric patient within a bore of a gantry (with the pediatric patient located outside the bore)
Figure 5:
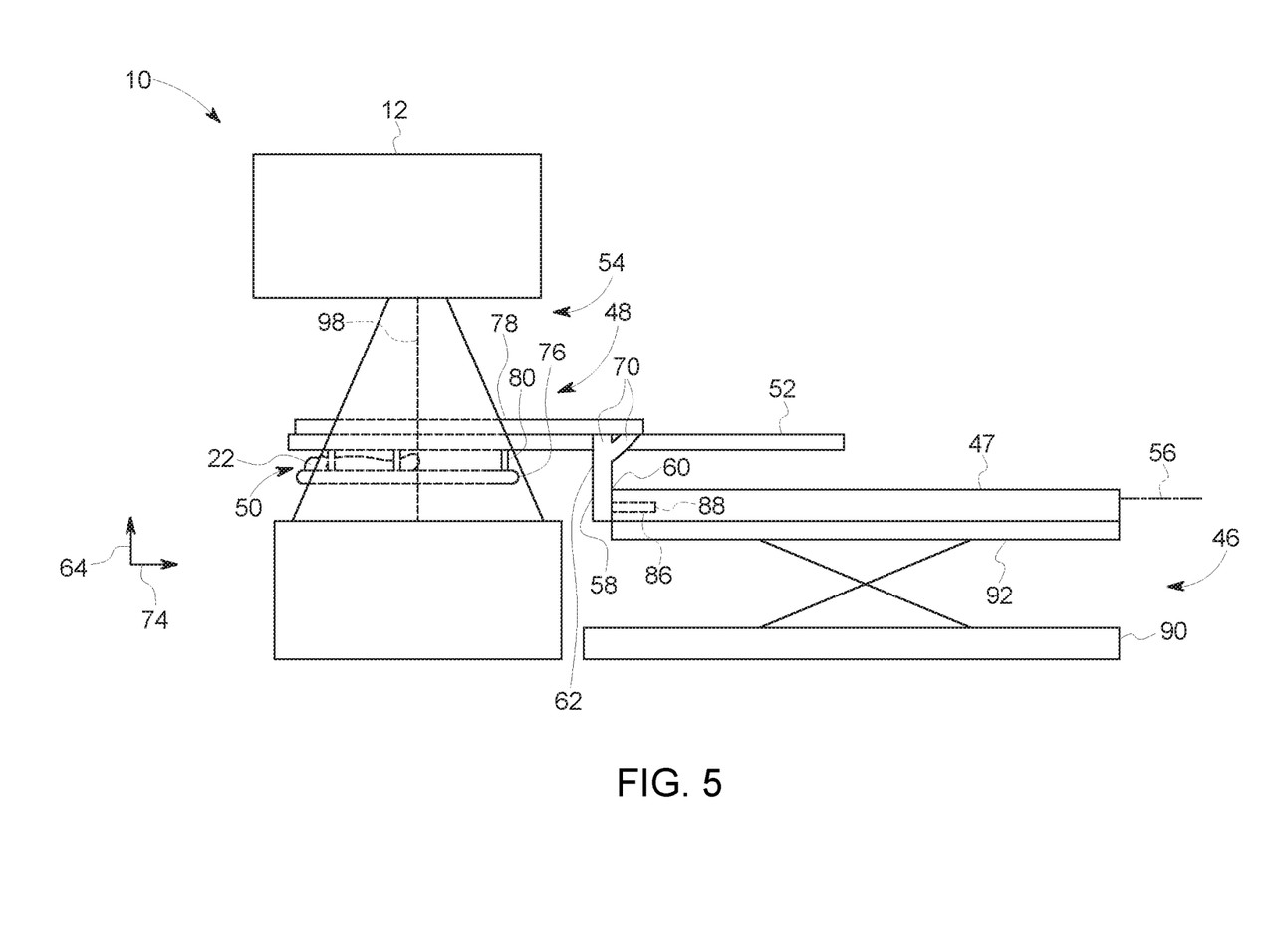
FIG. 5 is a schematic diagram of an embodiment of the pediatric patient support system of FIG. 2 being utilized to position a pediatric patient within a bore of a gantry (with the pediatric patient located within the bore)

FIG. 4 is a schematic diagram of an embodiment of the pediatric patient support system 48 of FIG. 2 being utilized to position the pediatric patient 22 within the bore 54 of the gantry 12 (with the pediatric patient 22 located outside the bore 54). As depicted, the pediatric patient 22 is disposed on the patient support 50 of the pediatric patient support system 48 (e.g., above the cradle 47) coupled to the end of the cradle 47 coupled to the table 46. The structure of the table 46 may vary. As depicted, the table 46 includes a table base 90 and an upper table 92 coupled to the table base 90. The cradle 47 is coupled to the table 46 (e.g., upper table 92). A height of the table 46 (or the upper table 92 relative to the table base 90) and thus the cradle 47 may be adjustable (e.g., via controller 44). The patient support 50 is configured to move (e.g., axially 74) relative to the cradle 47 and table 46 (e.g., manually, mechanically, or pneumatically). As depicted, a length 94 of the patient support 50 is less than a length 96 of the cradle 47. In certain embodiments, the length 94 is less than approximately 50 percent of the length 96. As depicted in FIG. 5, the patient 22 and the patient support 50 were axially 74 moved along the rods 52 into the bore 54 within a scan plane 98 of the gantry 12 for the imaging procedure.

Figure 6:
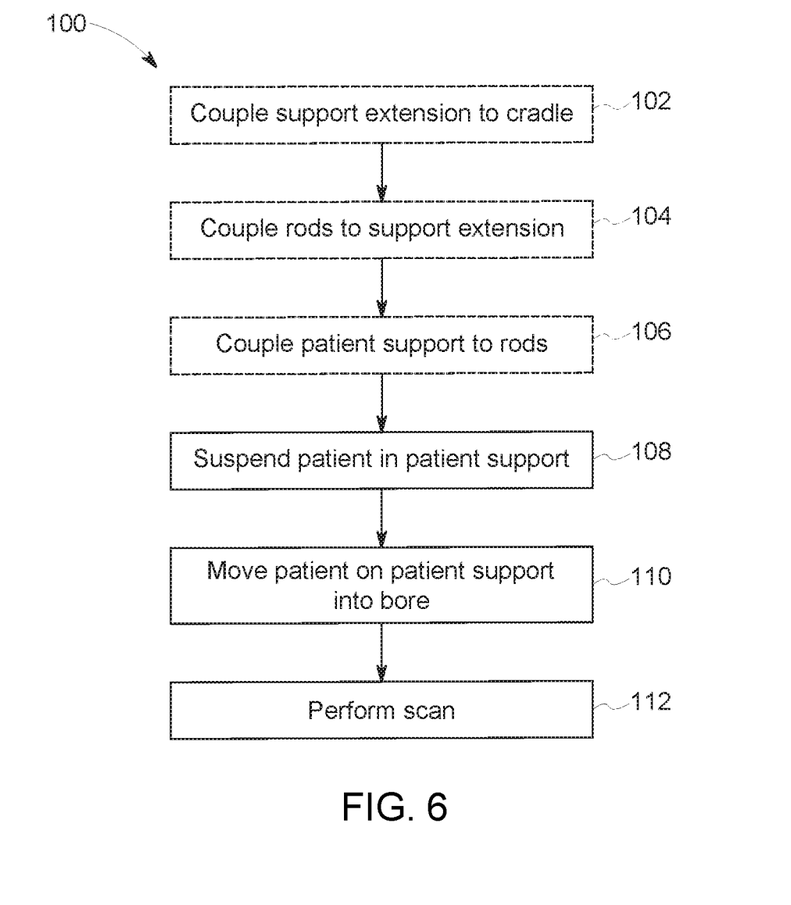
FIG. 6 is a flow chart of an embodiment of a method for utilizing the pediatric patient support system of FIG. 2 for imaging.

FIG. 6 is a flow chart of an embodiment of a method 100 for utilizing the pediatric patient support system of FIG. 2 for imaging. In certain embodiments, one or more of the steps of the method 100 may be performed in a different order than depicted in FIG. 6. The method 100 includes coupling the support extension 58 to the end 60 of the cradle 47 (block 102). In certain embodiments, coupling occurs via insertion of the protrusion 86 within the slot 88 disposed within the end 60 of the cradle 47. The method 100 also includes coupling respective rods 52 to the respective radial supports 62 of the support extension 58 so that a portion of the rods 52 extends into the bore 54 of the medical imaging system 10 (block 104). In certain embodiments, coupling the respective rods 52 to the respective radial supports 62 includes sliding the rods 52 through openings 72 of the supports 70. In certain embodiments, the respective rods 52 may also simultaneously be slid through openings in the stops 83 of the sliding mechanism 78 to couple the sliding mechanism 78 to the rods 52 so that the stops 83 are located on both sides of the radial supports 62. The method 100 further includes coupling the patient support 50 to the rods 52 (block 106). In certain embodiments, as noted above, this may include coupling the sliding mechanism 78 to the rods 52. Coupling the patient support 50 may also include coupling the backing 76 to the sliding mechanism 78 and/or the rods 52 as described above. The method 100 still further includes suspending or placing the pediatric patient 22 in the patient support 50 (e.g., backing 76) (block 108). It should be noted that steps 102-106 may not always be performed prior to step 108 as the pediatric patient support system 48 may already be assembled and coupled to the cradle 47. The method 100 even further includes axially moving the patient support 50 and the patient 22 along the rods 52 into the bore 52 of the medical imaging system 10 (block 110). The method 100 still further includes performing the imaging scan with the medical imaging system 10 on the patient 22 (block 112).

Technical effects of the disclosed embodiments include providing a pediatric patient support system that enables an infant or small toddler to be imaged with a reduced dose of radiation during an imaging procedure with a medical imaging system. For example, the pediatric patient support system may be coupled to an end of a cradle. The cradle solely supports the entire pediatric patient support system. The patient may be placed on a patient support of the pediatric patient support system and axially moved along rods into a bore of the medical imaging system so that the patient is suspended within the bore. During imaging, the table are located outside of the bore and the cradle remains outside of the path of the emitted radiation. This results in less material within the bore to attenuate the radiation. Thus, less radiation may be utilized to image the infant or small toddler to achieve the same image quality.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A pediatric patient support system comprising:
   a support extension configured to be removably coupled to an end of a cradle of a table, wherein the support extension comprises a pair of radial supports extending in a radial direction relative to a longitudinal axis of the cradle;
   a pair of rods, wherein each rod of the pair of rods is directly coupled at a location above the cradle to a respective upper end of a respective radial support of the pair of radial supports and extends substantially parallel to the longitudinal axis; and
   a patient support disposed between and coupled to the pair of rods, the patient support being configured to support a pediatric patient, wherein the patient support is configured to move axially relative to the longitudinal axis to move the pediatric patient in and out of a central bore of a medical imaging system, and the patient support is suspended from the pair of rods.

2. The pediatric patient support system of claim 1, wherein the pediatric patient support system is solely supported by the cradle of the table.

3. The pediatric patient support system of claim 2, wherein when the patient support is disposed within the central bore the end of the cradle remains outside a path of radiation emitted by a radiation source during imaging.

4. The pediatric patient support system of claim 1, wherein the pediatric patient support system is configured to attenuate between approximately 0 percent and approximately 10 percent of radiation emitted by a radiation source of the medical imaging system during an imaging procedure.

5. The pediatric patient support system of claim 1, wherein the patient support is removably coupled to the pair of rods.

6. The pediatric patient support system of claim 1, wherein the patient support is configured to be manually moved along the pair of rods.

7. The pediatric patient support system of claim 6, wherein the patient support comprises a sliding mechanism configured to slide along the pair of rods.

8. The pediatric patient support system of claim 1, wherein the patient support is configured to be mechanically moved along the pair of rods.

9. The pediatric patient support system of claim 1, wherein the pair of rods comprise carbon fiber tubes.

10. The pediatric patient support system of claim 1, wherein the patient support comprises a first length, the cradle comprises a second length, and the first length is less than approximately 50 percent of the second length.

11. The pediatric patient support system of claim 1, wherein each respective radial support of the pair of radial supports splits in the radial direction into a plurality of supports having respective openings to enable a respective rod to extend through.

12. The pediatric patient support system of claim 1, wherein the support extension comprises a protrusion configured to be disposed within a slot on the end of the cradle to couple the support extension to the cradle.

13. A method for utilizing a pediatric patient support system, comprising:
coupling a support extension to an end of a cradle of a table, wherein the support extension comprises a pair of radial supports extending in a radial direction relative to a longitudinal axis of the cradle;
directly coupling a respective rod at a location above the cradle to a respective upper end of each radial support of the pair of radial supports so that each respective rod extends substantially parallel to the longitudinal axis; and
coupling a patient support to each respective rod so that the patient support is disposed between the respective rods, the patient support being configured to support a pediatric patient, wherein the patient support is configured to move axially relative to the longitudinal axis to move the pediatric patient in and out of a central bore of a medical imaging system, and the patient support is suspended from the respective rods.

14. The method of claim 13, comprising axially moving the patient support while supporting the pediatric patient along the respective rods into the central bore for an imaging procedure.

15. The method of claim 13, wherein axially moving the patient support comprises manually moving the patient support along the respective rods.

16. The method of claim 13, wherein axially moving the patient support comprises mechanically moving the patient support along the respective rods.

17. The method of claim 13, wherein the support extension, the respective rods, and the patient support are solely supported by the cradle of the table.

18. The method of claim 13, wherein when the patient support is disposed within the central bore the end of the cradle remains outside a path of radiation emitted by a radiation source during imaging.

19. The method of claim 13, wherein coupling the support extension comprises disposing a protrusion of the support extension within a slot on the end of the cradle, and coupling the respective rod to each radial support of the pair of radial supports comprises sliding the respective rod through openings in the respective radial support.

20. A pediatric patient support system comprising:
a support extension configured to be removably coupled to an end of a cradle of a table via a protrusion of the support extension being inserted within a slot in the end of the cradle, wherein the support extension comprises a pair of radial supports extending above the cradle in a radial direction relative to a longitudinal axis of the cradle;
a pair of rods configured to partially extend into a central bore of a medical imaging system when the pediatric patient support system is coupled to the cradle, wherein each rod of the pair of rods at a location above the cradle extends through a respective upper end of a respective radial support of the pair of radial supports and extends substantially parallel to the longitudinal axis; and
a patient support disposed between and coupled to the pair of rods, the patient support being configured to support a pediatric patient, wherein the patient support is configured to move axially relative to the longitudinal axis along the pair of rods to move the pediatric patient in and out of the central bore, and the patient support is suspended from the respective rods;
wherein the support extension, the pair of rods, and the patient support are configured to be solely supported by the cradle of the table.

* * * * *